United States Patent [19]
Bird et al.

[11] Patent Number: 5,442,052
[45] Date of Patent: Aug. 15, 1995

[54] EXPRESSION OF GENES IN TRANSGENIC PLANTS

[75] Inventors: Colin R. Bird, Bracknell; Donald Grierson, Shepshed; Wolfgang W. Schuch, Heathlake Park, all of England

[73] Assignee: Zeneca Limited, London, England

[21] Appl. No.: 50,393

[22] PCT Filed: Nov. 7, 1991

[86] PCT No.: PCT/GB91/01956
 § 371 Date: Jul. 8, 1993
 § 102(e) Date: Jul. 8, 1993

[87] PCT Pub. No.: WO92/08798
 PCT Pub. Date: May 29, 1992

[30] Foreign Application Priority Data

Nov. 8, 1990 [GB] United Kingdom ............... 9024323

[51] Int. Cl.[6] ............... C07H 21/04; C12N 5/14; C12N 15/82; A01H 5/00
[52] U.S. Cl. ............... 536/24.1; 536/24.5; 435/69.1; 435/70.1; 435/172.3; 435/240.4; 435/320.1; 800/205; 800/250
[58] Field of Search ............... 536/24.1, 24.5; 435/69.1, 70.1, 172.3, 240.4, 320.1; 800/205, 250

[56] References Cited

FOREIGN PATENT DOCUMENTS 271988 6/1988 European Pat. Off. .
9109128 6/1991 WIPO .
8912386 12/1992 WIPO .

OTHER PUBLICATIONS

Bird et al., "The tomato polygalacturonase gene and ripening—specific expression in transgenic plants" Plant Molecular Biology, vol. 11, 1988, pp. 651–662—see the whole document.
Shabbeer et al., "Putatuve regulatory factors binding a fruit ripening promoter", Biological Abstracts BR39;65917 see the abstract, vol. 41, 1990 P5–6.
Cordes et al. 1989, Plant Cell 1(10):1025–1034.
Thornburg et al. 1987 Proc. Natl. Acad. Sci. USA 84(3):744–748.
Lewin, R. 1987, Science 237:1570.
Reeck et al. 1987 Cell 50:667.

*Primary Examiner*—David T. Fox
*Attorney, Agent, or Firm*—Cushman Darby & Cushman

[57] ABSTRACT

DNA construct for use in transforming plant cells comprises and exogenous gene with upstream promoter and downstream terminator sequences, the promoter being a DNA sequence of not less than about 5 kilobases homologous to the DNA control sequence found upstream of the tomato PG gene. Preferably the terminator is homologous to the DNA control sequence of about 1.6 kilobases found downstream of the tomato polygalacturonase gene. Enhanced expression of the exogenous gene is obtained. The invention also included plant cells containing such constructs and plants derived therefrom.

8 Claims, 3 Drawing Sheets

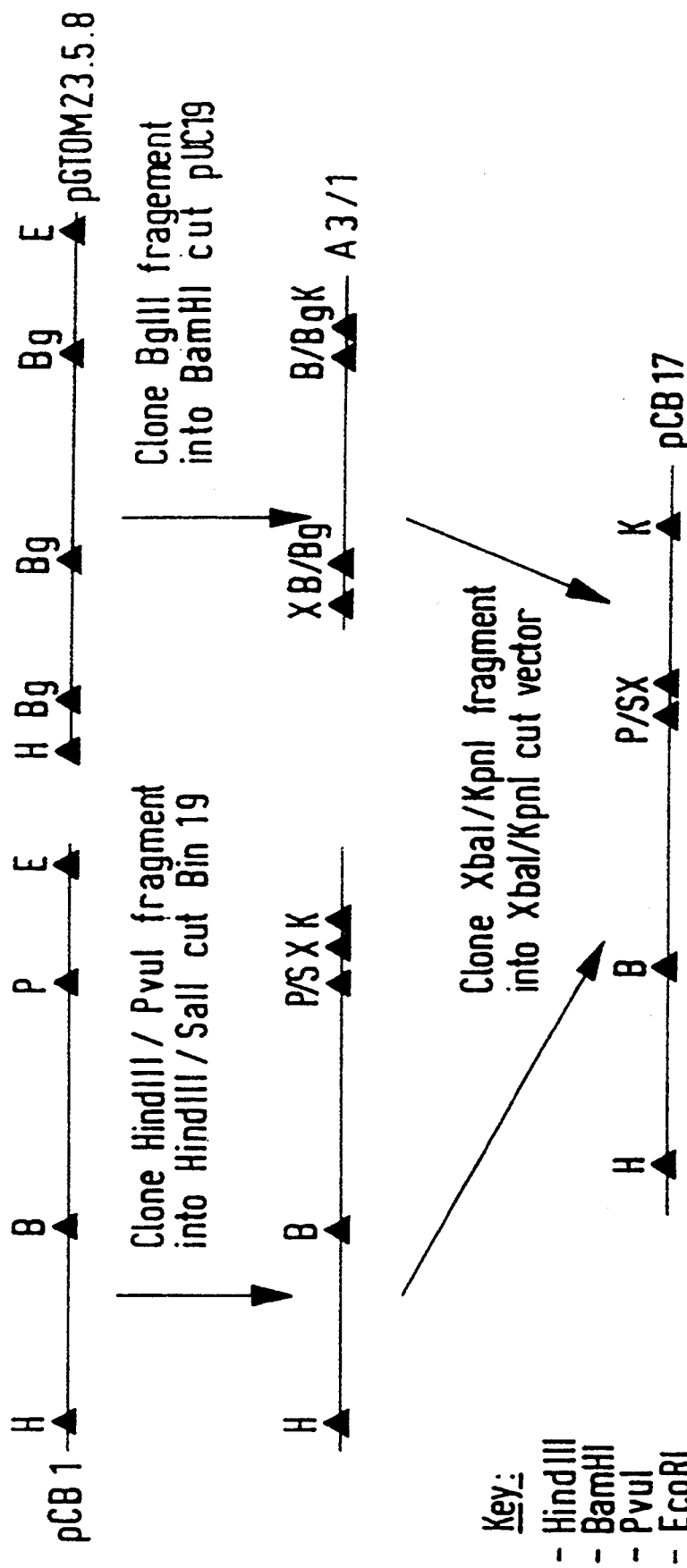

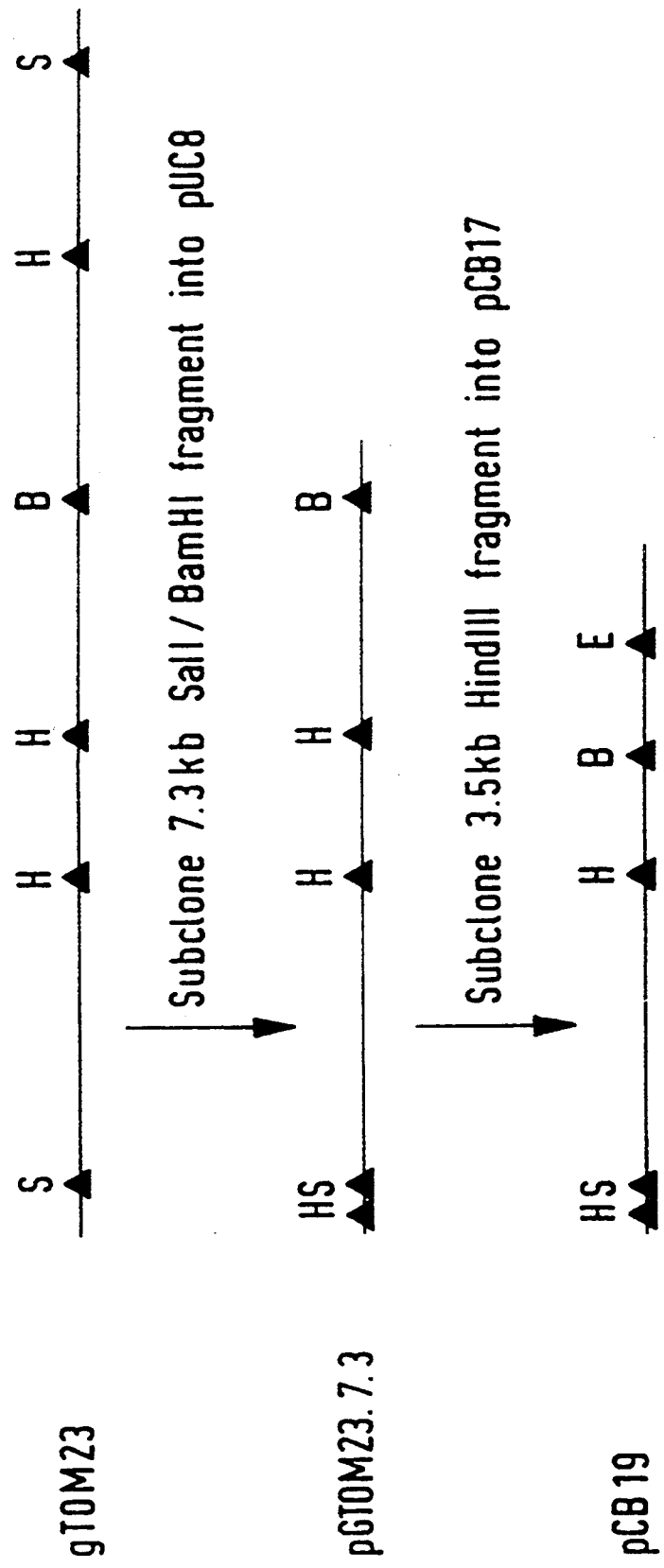

EXPRESSION OF GENES IN TRANSGENIC PLANTS

FIELD OF THE INVENTION

The present invention relates to the expression of genes in transgenic plants. In particular it describes the isolation and use of DNA sequences which permit a high level of expression of foreign genes in transgenic plants.

BACKGROUND OF THE INVENTION

The ability to isolate and manipulate plant genes has opened the way to gain understanding about the mechanisms involved in the regulation of plant gene expression. This knowledge is important for the exploitation of genetic engineering techniques, applied to problems such as the expression of genes in genetically manipulated crop plants. A large number of examples are now in the literature of plant DNA sequences which have been used to drive the expression of foreign genes in plants. In most instances the regions immediately 5' to the coding regions of genes have been used in gene constructs. These regions are referred to as promoter sequences. They may be derived from plant DNA; or from other sources, e.g., viruses. It has been demonstrated that sequences up to 500–800 bases in most instances are sufficient to allow for the regulated expression of foreign genes. This regulation has involved tissue-specificity; regulation by external factors such as light, heat treatment, chemicals and hormones; and developmental regulation.

These experiments have been carried out using gene fusions between the promoter sequences and foreign genes such as bacterial promoter genes, etc.

Although regulation has been observed this has been hampered by two factors:

1. The low level of expression observed for the transgene in comparison with the endogenous gene. In most instances expression of the transgene has been approximately 1-10% of the expression achieved when the same promoter drives the endogenous gene. This has led to the suggestion that sequences internal to genes may also be important for efficient expression. This has been supported by experiments in which complete genes including 5' and 3' regions as well as coding regions have been used in blot transformation experiments. The influence of sequences surrounding the introduced transgene on the level of expression which can be achieved is normally referred to as 'position effect'. For practical purposes it is desirable that gene constructs introduced into plants give expression levels comparable with that of an endogenous gene. In practice, promoters may be chosen for gene constructs because of their induction pattern, e.g. their tissue specificity or temporal pattern of expression. However, the level of expression of the transgene is usually critical; if the desired promoter cannot give a high enough level of expression it will not be useful.

2. Great variation exists in the level of expression of transgenes between different transformed plant lines. It is not clear why this should be so: it may be another manifestation of the "position effect". These expression levels can differ by as much as two orders of magnitude. Thus a large number of transformants may need to be analysed before one exhibiting the desired expression level can be identified.

These two factors make it very costly and time-consuming to use known promoter constructs for practical genetic plant engineering.

SUMMARY OF THE INVENTION

The object of the present invention is to provide novel plant gene constructs which when used to transform plant cells give a high and reliable expression of the inserted gene.

DETAILED DESCRIPTION OF THE INVENTION

Figure 1:
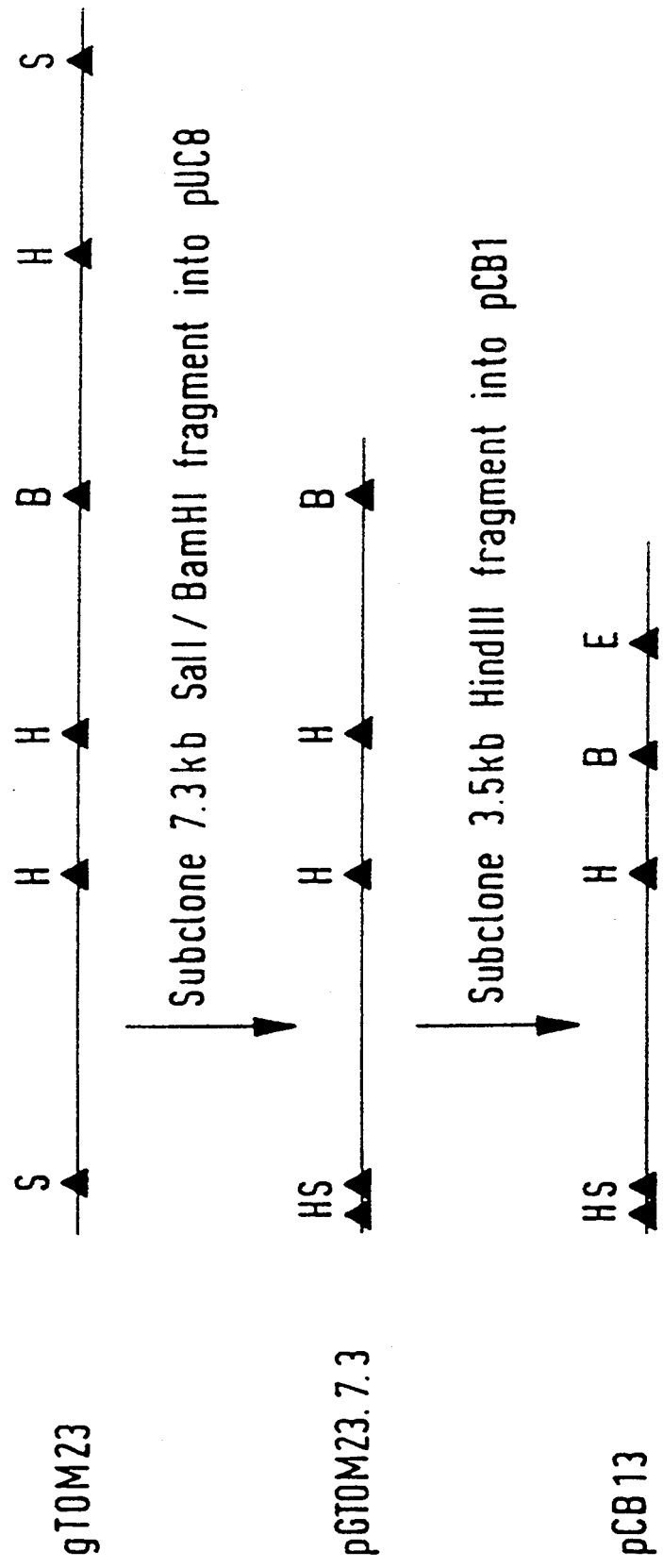

According to the present invention we provide a DNA construct for use in transforming plant cells which comprises an exogenous gene under the control of upstream promoter and downstream terminator sequences, characterised in that the upstream promoter is a DNA sequence of not less than about 5 kilobases that is homologous to the DNA control sequence found upstream of the tomato polygalacturonase gene. Preferably that the downstream terminator is a DNA sequence that is homologous to the DNA control sequence of about 1.6 kilobases found downstream of the tomato polygalacturonase gene. We further provide plant cells transformed with such constructs, and plants containing or composed of such cells.

By the term 'exogenous gene' we indicate a stretch of DNA adapted to be transcribed into functional RNA under the action of plant cell enzymes such as RNA polymerase. Functional RNA is RNA which affects the biochemistry of the cell: it may for example be mRNA which is translated into protein by ribosomes; or antisense RNA which inhibits the translation of mRNA complementary to it into protein. In principle all kinds of exogenous genes are useful in the present invention. The gene may for example be a marker gene such as gus; a gene coding for an insecticidal protein such as the δ-endotoxin from *Bacillus thuringiensis*; or a gene conferring herbicide resistance, e.g. to glyphosate or to a herbicide inhibiting the ALS pathway. A very wide variety of functional exogenous genes is known from the literature, and the present invention is applicable to these as well as to many others. As well as functional genes, the exogenous gene may code for other types of functional RNA: for example antisense RNA complementary to any kind of mRNA produced by the plant cell: for example, antisense RNA complementary to mRNA from fruit ripening genes such as polygalacturonase. It is also found that the expression or translation of full-length mRNA of certain genes can be interfered with by expression of truncated RNAs ("sense RNA") having the same sequence as part of the gene. The present invention may be used to generate such 'sense RNA' and thereby downregulate.

Plant cells according to the invention may be transformed with constructs of the invention according to a variety of known methods (Agrobacterium Ti plasmids, electroporation, microinjection, etc.). The transformed cells may then in suitable cases be regenerated into whole plants in which the new nuclear material is stably incorporated into the genome. Both transformed monocot and dicot plants may be obtained in this way, although the latter are usually more easy to regenerate.

In work leading to the present invention we have found that sequences upstream of the polygalacturonase (PG) gene permit the regular expression of foreign genes in tomato plants at a high level. We have previously described the isolation of overlapping clones of tomato DNA isolated from a genomic library established in EMBL3 bacteriophage. We have also disclosed the isolation of a 1.45 KG promoter fragment which gives fruit-specific and ripening-specific expression of foreign genes in tomato (Bird et al, Plant Mol. Biol. 11, pp 651–662, 1988). We have now constructed a series of additional vectors, one of which has given high levels of expression of a foreign gene in tomato fruit. The expression levels obtained are of the same order as those obtained for the endogenous PG gene. This represents a major improvement over expression levels obtained previously.

ment from A3/1. After transformation, one clone with the correct insert was designated pCB17 (FIG. 2).

The correct construction of pCB17 was checked by nucleotide sequence analysis of the plasmid DNA at the boundary between the CAT gene and the PG 3' fragment. An unexpected region of the Bin19 polylinker was found to have remained at this junction. This was judged to be unlikely to interfere with the correct functioning of the plasmid. The sequence of pCB17 in this region is:

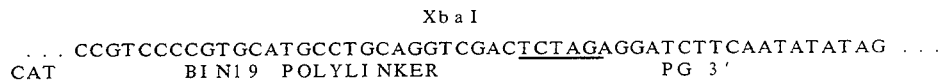

BRIEF DESCRIPTIONS OF THE DRAWINGS

The invention will be further described with reference to the drawings, in which:

FIG. 1 is a diagram of DNA vector pCB13;
FIG. 2 is a diagram of DNA vector pCB17;
FIG. 3 is a diagram of DNA vector pCB19.

The following Examples illustrate the invention.

EXAMPLE 1

A. Construction of pCB13.

The PG (polygalacturonase) promoter region in plasmid pCB1 (Bird et al Plant Molecular Biology 11,651–662, 1988) was extended by the addition of a 3.5 KG fragment from genomic clone gTOM23 (deposited on 5 December 1986 at the National Collections of Industrial and Marine Bacteria, Aberdeen, Scotland, NCIMB Accession Number 12373). The 7.3 KB SalI/BamHI fragment adjacent to the left arm of lambda EMBL3 in gTOM23 was cloned into the SalI/BamHI sites of pUC8 to give plasmid pGTOM23.7.3. The 3.5 kb HindIII fragment from pGTOM23.7.3 was isolated and cloned into the HindIII site of pCB1. Plasmids with the correct orientation of the 3.5 kb HindIII insert contained a 4.9 kb SalI/BamI fragment. One such clone was designated pCB13 (FIG. 1).

B. Construction of pCB17.

A 1.6 kb region from the 3' end of the tomato PG gene was substituted for the nopaline synthase polyadenylation sequence in pCB1 (Bird et al Plant Molecular Biology 11, 651–662, 1988).

The 5.8 kb SalI/BamHI fragment adjacent to the right arm of lambda EMBL3 in gTOM23 was cloned into the SalI/BamHI sites of pUC8 to give plasmid pGTOM23.5.8. The 1.6 kb BglII fragment from pGTOM23.5.8 was isolated and cloned into the BamHI site of pUC19. Plasmids with the correct orientation of the 1.6 kb BglII insert contained a 550 bp XbaI/BstEII fragment. One such clone was designated A3/1.

A 2.2 kb HindIII/PvuI was isolated as a fragment from pCB1. This contained a 1.45 kb PG promoter fragment and the chloramphenicol acetyl transferase (CAT) gene. This was cloned into Bin19 (Bevan, Nucleic Acids Research, 1984, 12, 8711–8721) which had been cut with SalI followed by filling of the cohesive ends with T4 DNA polymerase and subsequently digested with HindIII. Plasmids with the 2.2 kb HindIII/PvuI fragment contained a 2.2 kb HindIII/XbaI fragment. One of these clones was digested with XbaI and KpnI and ligated with the 1.6 kb XbaI/KpnI frag- The PG promoter region in plasmid pCB17 was extended by the addition of a 3.5 kb fragment from genomic clone gTOM23 (NCIMB Accession Number 12373).

The 3.5 kb HindIII fragment from pGTOM23.7.8 was cloned into the HindIII site in pCB17. Plasmids with the correct orientation of the 3.5 kb Hind AYE insert contained a 4.9 kb SalI/BamI fragment. One such clone was designated pCB19 (FIG. 3). This is a construct according to the present invention.

EXAMPLE 2

Generation of transformed plants

The vectors pCB13, pCB17 and pCB19 were transferred to *Agrobacterium tumefaciens* LBA 4404 (a micro-organism widely available to plant biotechnologists) and were used to transform tomato plants. Transformation of tomato stem segments followed standard protocols (e.g., (Bird et al Plant Molecular Biology 11, 651–662, 1988). Transformed plants were identified by their ability to grow on media containing the antibiotic kanamycin. Plants were regenerated and grown to maturity. Ripening fruit were analysed for expression of the CAT gene (Bird et al Plant Molecular Biology 11, 651–662, 1988).

Table 1 shows the results of a comparison of plants transformed with the previously defined PG promoter (Bird et al., Plant Molecular Biology 11, 651–662, 1988) and plants transformed with the newly described vectors.

TABLE 1

| | CAT Expression In Transgenic Plants | | |
|---|---|---|---|
| VECTOR | PROMOTER | 3' END | CAT units/mg protein |
| pCB1 | 1.45 Kb | nos | 0.66 |
| pCB13 | 5 Kb | nos | 0 |
| pCB17 | 1.45 Kb | 1.8 kb PG | 0.85 |
| pCB19 | 5 Kb | 1.8 Kb PG | 1456 |

Measurements of CAT and PG mRNA indicated that the level of CAT protein expression is of the same order of magnitude as PG expression.

We claim:

1. DNA construct for use in transforming plant cells which comprises a structural gene under the control of upstream promoter and downstream terminator sequences, characterized in that the structural gene is other than tomato polygalacturonase, the upstream promoter is a 4.9 SalI/BamI kilobase fragment of the DNA control sequence found upstream of the tomato polygalacturonase structural gene, and the downstream terminator sequence is a 1.6 kilobase BglII fragment of the DNA control sequence found downstream of the tomato polygalacturonase structural gene, said fragments being obtainable from the genomic clone gTOM23, deposited at the National Collections of Industrial and Marine Bacteria under the accession number NCIMB 12373.

2. Construct as claimed in claim 1 in which the structural gene codes for an insecticidal protein.

3. Construct as claimed in claim 1 in which the structural gene generates antisense RNA.

4. A plant cell comprising a DNA construct claimed in any of claims 1, 2, or 3 and adapted to transcribe RNA from the structural gene.

5. A plant cell as claimed in claim 4 in which the RNA transcribed is mRNA which is subsequently translated by the cell into protein.

6. A plant cell as claimed in claim 4 in which the RNA transcribed inhibits production of a protein produced by the cell.

7. A plant cell as claimed in claim 6 in which the RNA transcribed is antisense to the mRNA of the protein of which production is inhibited.

8. Plants comprising cells which comprise a DNA construct as claimed in claim 1 which is stably integrated into the plant genome and adapted to transcribe RNA, wherein either the RNA transcribed is mRNA which is subsequently translated by the cell into protein, or the RNA transcribed inhibits production of a protein produced by the cell, or the RNA transcribed is antisense to the mRNA of the protein of which production is inhibited; and seeds and progeny thereof.

* * * * *